(12) United States Patent
Cerda

(10) Patent No.: US 7,485,435 B2
(45) Date of Patent: *Feb. 3, 2009

(54) SIMULTANEOUS DETECTION OF METABOLIC ENZYME ACTIVITY AND METABOLITE LEVELS

(75) Inventor: Blas Cerda, Milford, MA (US)

(73) Assignee: PerkinElmer LAS, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/539,180

(22) PCT Filed: Feb. 28, 2005

(86) PCT No.: PCT/US2005/006371

§ 371 (c)(1),
(2), (4) Date: Mar. 20, 2006

(87) PCT Pub. No.: WO2006/025863

PCT Pub. Date: Mar. 9, 2006

(65) Prior Publication Data

US 2006/0257963 A1 Nov. 16, 2006

(30) Foreign Application Priority Data

Aug. 30, 2004 (WO) .................... PCT/US04/28238

(51) Int. Cl.
*C12Q 1/34* (2006.01)
*G01N 33/00* (2006.01)

(52) U.S. Cl. .......................................... 435/18; 436/86
(58) Field of Classification Search ........................ None
See application file for complete search history.

(56) References Cited

U.S. PATENT DOCUMENTS

| | | | |
|---|---|---|---|
| 5,096,812 A | 3/1992 | Rachel et al. | |
| 5,629,210 A | 5/1997 | Hercules et al. | |
| 5,719,035 A | 2/1998 | Rosenthal et al. | |
| 6,258,605 B1 | 7/2001 | Chace | |
| 6,455,321 B1 | 9/2002 | Chace | |
| 6,670,194 B1 | 12/2003 | Aebersold et al. | |
| 2003/0199102 A1 | 10/2003 | Ostrup | |
| 2005/0048499 A1 | 3/2005 | Cerda | |

FOREIGN PATENT DOCUMENTS

WO    WO 00/26677    5/2000

OTHER PUBLICATIONS

Merck Manual Home Edition:Acid-Base Balance: Alkalosis, Disorders of Nutrition and Metabolsim (2007) http://www.merck.com/mmhe/sec12/ch159/ch159c.html.*
Gahl et al. CYSTINOSIS; New England Journal of Medicine, vol. 347, No. 2 (2002) pp. 111-121.*
Gerber et al. Direct Profiling of Multiple Enzyme Activities in Human Cell Lysates by Affinity Chromatography/Electrospray Ionization Mass Spectrometry: Application to Clinical Enzymology; Analytical Chemistry, vol. 73, No. 8 (2001) pp. 1651-1657.*
Chace et al. Electrospray Tandem Mass Spectrometry for Analysis of Acylcarnitines in Dried Postmortem Blood Specimens Collected at Autopsy From Infants With Unexplained Cause of Death; Clinical Chemistry, vol. 47, No. 7 (2001) pp. 1166-1182.*
Roe et al. Recent Developments in the Investigation of Inherited Metabolic Disorders Using Cultured Human Cells; Molecular Genetics and Metabolism, vol. 68 (1999) pp. 243-257.*
Guerra-Giraldez et al. Compartmentation of Enzymes in a Microbody, The Glycosome, is Essential in Trypanosoma Brucei; Journal of Cell Science, vol. 115 (2002) pp. 2651-2658.*
B. Cerda, H. Sterling; "Assay for Biotinidase Deficiency by Tandem Mass Spectrometry," May 2004 Newborn and Genetic Testing Symposium.
Online Mendelian Inheritance in Man (OMIM) entry for Zellweger syndrome. 2005. Accessed1 Nov. 29, 2006; 13 pages.
OMIM entry for Kears-Sayre syndrome. 2006. Access online Nov. 29, 2006. 13 pages.
J.O. Sass et al., "Mutations in ACY1, the Gene Encoding Aminoacylase 1, Cause a Novel Inborn Error of Metabolism," Am. J. Hum. Genet. 2006, 78:401-409.
K.L. Peterson, D.K. Srivastava; "Functional role of a distal (3'-phosphate) group of CoA in the recombinant human liver medium-chain acyl-CoA dehydrogenase-catalysed reaction," Biochem. J 325: 751-60, 1997.
R. Ramsay et al., "Carnitine palmitoyltransferase in human erythrocyte membrane," Biochem. J., 1991, vol. 275, pp. 685-688.
Definition of "metabolism," 1991. Webster's College Dictionary, Random House, p. 851.

(Continued)

*Primary Examiner*—Jon P Weber
*Assistant Examiner*—Paul C. Martin
(74) *Attorney, Agent, or Firm*—Gifford, Krass, Sprinkle, Anderson & Citkowski, P.C.

(57) ABSTRACT

Provided are methods for detecting a metabolic disorder in an individual using mass spectrometry. One method involves (a) contacting a sample containing (i) one or more metabolically indicative enzymes and (ii) one or more metabolic analytes, with one or more substrates for said one or more enzymes to produce a reaction admixture, under conditions wherein at least one of said enzymes is capable of acting on a corresponding substrate to generate at least one product, and wherein one or more protease inhibitors are present; (b) contacting said reaction admixture with a reagent that inhibits the ability of said one or more enzymes to act on a corresponding substrate, wherein said one or more metabolic analytes and said at least one product are soluble in said reagent; to produce a test sample and (c) determining the presence or amount of said one or more metabolic analytes and said at least one product contained in said test sample using mass spectrometry, wherein a determined presence or amount of said one or more metabolic analytes and said at least one product correlates with presence or absence of said metabolic disorder. product correlates with presence or absence of said metabolic disorder.

23 Claims, 1 Drawing Sheet

OTHER PUBLICATIONS

P. Rinaldo et al.; "Disorders of fatty acid transport and mitochondrial oxidation: Challenges and dilemmas of metabolic evaluation," Nov./Dec. 2000, vol. 2, No. 6, pp. 338-344.

P. Rinaldo et al., "Fatty Acid Oxidation Disorders," Annu. Rev. Physiol., 2002, 64: 477-501.

M. McCaman et al., "Fluorimetric Method for the Determination of Phenylalanine in Serum," J. Lab. Clin. Med., vol. 59, No. 5, Aug. 1961, pp. 885, 887, 889.

N. Chamoles et al., "Hurler-like Phenotype: Enzymatic Diagnosis in Dried Blood Spots on Filter Paper," Clinical Chemistry, 47:12, pp. 2098-2102, 2001.

N. Chamoles et al., Fabry Disease: Enzymatic Diagnosis in Dried Blood Spots on Filter Paper, Clinica Chemica Acta 308, 2001, p. 195-196.

L. Sweetman, Newborn Screening by Tandem Mass Spectrometry (MS-MS), Clinical Chemistry, vol. 47, No. 11, 2001, pp. 1937-1938.

A. Fujimoto et al., Quantitative Beutler Test for Newborn Mass Screening of Galactosemia Using a Fluorometric Microplate Reader, Clinical Chemistry 46:6, 2000, pp. 806-810.

D. Chace, "Rapid diagnosis of homocystinuria and other hypermethioninemias from newborns' blood spots by tandem mass spectrometry," Clinical Chemistry, 42:3, 1996, pp. 349-355.

B. Im et al., "Bacterial Degradation of Biotin," vol. 248, No. 22, Nov. 1973, pp. 7798-7805.

Non-Final Office Action for U.S. Appl. No. 10/539,273, Sep. 19, 2008.

\* cited by examiner

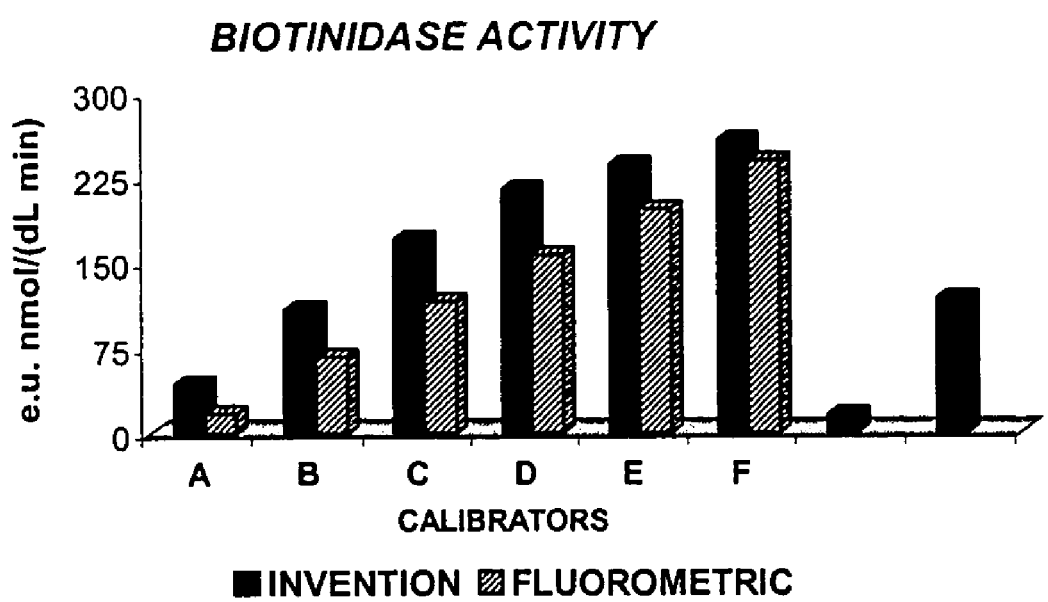

SIMULTANEOUS DETECTION OF METABOLIC ENZYME ACTIVITY AND METABOLITE LEVELS

REFERENCE TO RELATED APPLICATIONS

This application is a U.S. national phase of PCT/US52005/006371, filed Feb. 28, 2005, which claims priority to PCT/US2004/028238, filed Aug. 30, 2004. which claims priority to U.S. patent application Ser. No. 10/652,732, filed Aug. 29, 2003, the entire content of all of which are incorporated herein by reference.

BACKGROUND

The present invention relates generally to diagnostic medicine and more specifically to methods for diagnosing metabolic disorders.

Metabolism is the process of building the body's molecular structures from nutrients (anabolism) and breaking them down for energy (catabolism). Metabolic processes result in growth, produce energy, eliminate wastes, and control distribution of nutrients in the body. Homeostasis, or a steady state, in the body is a result of normal metabolism.

Enzymes play an important role in metabolism because they catalyze conversion of one molecule to another during metabolic processes. When a metabolic enzyme is faulty or present in an abnormal amount in an individual, a metabolic disorder can result. Metabolic disorders are frequently due to genetic inheritance that leads to absence or overproduction of an enzyme or production of a faulty enzyme.

As an example, deficiencies produced by an inactive gene can prevent the body from making an enzyme (or enzymes) needed to break down certain amino acids or types of fats. Such an enzyme deficiency typically prevents normal metabolism of a nutrient, causing the nutrient or its metabolite to build up in the body to toxic levels. An enzyme deficiency can also cause nutrient deficiencies when an enzyme is unable to make a normal end-product of a metabolic process. Nutrient deficiencies resulting from metabolic disorders can lead to impaired growth and development, and other severe health problems.

Many inherited metabolic disorders are fatal in the first weeks or months of postnatal life, for example, severe defects in the conversion of pyruvate to acetyl coenzyme A (CoA), some urea cycle defects, and severe defects in the processing of fructose. Infants and children with a treatable metabolic disorder are often identified by newborn screening in developed countries. For example, testing for phenylketonurea is routine practice in developed countries. Phenylketonurea is an example of a relatively common inherited metabolic disorder and it occurs in about one out of 16,000 live births in the United States. Individuals having phenylkentonuria do not produce the enzyme necessary to break down phenylalanine (an amino acid). Fortunately, when recognized, this metabolic disorder can be successfully treated by dietary restriction.

Unfortunately, newborns are not typically screened for other metabolic disorders such as homocysteinuria, maple syrup urine disease, organic acid disorders, and disorders of fatty acid oxidation. As a result, these disorders are often detected in infants and children after damage has occurred and effects such as developmental delay and mental retardation become apparent. However, such effects often can be reduced or avoided with early detection and sustained dietary restriction. Such early detection involves examining a blood sample for an enzyme activity or a metabolic marker (a metabolite).

Wide-spread newborn testing for multiple inherited metabolic disorders has been unavailable due, in part, to cost associated with each test. One approach for reducing costs is to examine multiple enzyme activities and metabolites and in a single test. However, development of multi-enzyme/metabolite testing has been hindered by the different conditions needed for enzyme tests in comparison to metabolite tests. Currently, enzyme and metabolite tests cannot be carried out simultaneously from a single patient sample.

Thus, there exists a need for methods for efficiently diagnosing a metabolic disorder in an individual. The present invention satisfies this need and provides related advantages as well.

SUMMARY

The present invention provides a method for detecting a metabolic disorder in an individual. The method involves (a) contacting a sample containing (i) one or more metabolically indicative enzymes and (ii) one or more metabolic analytes, with one or more substrates for said one or more enzymes to produce a reaction admixture, under conditions wherein at least one of said enzymes is capable of acting on a corresponding substrate to generate at least one product, and wherein one or more protease inhibitors are present; (b) contacting said reaction admixture with a reagent that inhibits the ability of said one or more enzymes to act on a corresponding substrate, wherein said one or more metabolic analytes and said at least one product are soluble in said reagent; to produce a test sample and (c) determining the presence or amount of said one or more metabolic analytes and said at least one product contained in said test sample using mass spectrometry, wherein a determined presence or amount of said one or more metabolic analytes and said at least one product correlates with presence or absence of said metabolic disorder. A sample used in a method of the invention can be, for example, a body fluid sample, such as blood, and can be obtained from a neonate, newborn, child or adult. In one embodiment, the method can include, in step (a) contacting the sample with one or more reference substrates. In another embodiment, the method can include, in step (b), contacting the sample with one or more reference products. In a further embodiment, the method can include, in step (d), prior to determining, adding one or more reference products corresponding to the at least one product. In yet another embodiment, the method can include, in step (d), prior to determining, adding one or more reference analytes corresponding to the one or more metabolic analytes contained in the sample.

The invention provides another method for detecting a metabolic disorder in an individual. The method involves (a) contacting a vessel containing one or more substrates in dried form with a sample from the individual, the sample containing (i) one or more metabolically indicative enzymes and (ii) one or more metabolic analytes, in aqueous solution; under conditions wherein at least one of the enzymes is capable of acting on a corresponding substrate to generate at least one product, and wherein one or more protease inhibitors are present; (b) adding a reagent that inhibits the ability of the one or more enzymes to act on a corresponding substrate, and wherein the one or more metabolic analytes and at least one product are soluble in the reagent; (c) determining the presence or amount of the one or more metabolic analytes and the at least one product in the resultant mixture using mass spectrometry, wherein a determined presence or amount of said one or more metabolic analytes and said at least one product correlates with presence or absence of said metabolic disorder. A sample used in a method of the invention can be, for example, a body fluid sample, such as blood, and can be obtained from a neonate, newborn, child or adult. In an embodiment, the vessel further can contain one or more reference substrates, one or more metabolic analytes, one or more references products, or a combination of such references.

The invention provides a further method for detecting a metabolic disorder in an individual. The method involves (a) contacting a sample comprising: (i) one or more metabolically indicative enzymes and (ii) one or more metabolic analytes, with one or more substrates for the one or more enzymes to produce a reaction admixture, under conditions wherein at least one of the enzymes is capable of acting on a corresponding substrate to generate at least one product, and wherein one or more protease inhibitors are present; (b) contacting the reaction admixture with a reagent that inhibits the ability of the one or more enzymes to act on a corresponding substrate, wherein the one or more metabolic analytes and the at least one product are soluble in the reagent, to produce a test sample; (c) contacting the reaction admixture with one or more reference products and one or more reference analytes, and (d) determining the presence or amount of the one or more metabolic analytes and the at least one product contained in the test sample, with respect to the one or more reference products and one or more reference analytes, using mass spectrometry, wherein a determined presence or amount of the one or more metabolic analytes and the at least one product correlates with presence or absence of the metabolic disorder.

Another method for detecting a metabolic disorder in an individual involves (a) contacting a vessel containing one or more substrates in dried form with a sample from the individual, the sample containing (i) one or more metabolically indicative enzymes and (ii) one or more metabolic analytes, (b) contacting the vessel with a solution to generate conditions wherein at least one of the enzymes is capable of acting on a corresponding substrate to generate at least one product, and wherein one or more protease inhibitors are present; (c) adding a reagent that inhibits the ability of the one or more enzymes to act on a corresponding substrate, wherein the one or more metabolic analytes and at least one product are soluble in the reagent; (d) determining the presence or amount of the one or more metabolic analytes and the at least one product in the resultant mixture using mass spectrometry, wherein a determined presence or amount of the one or more metabolic analytes and the at least one product correlates with presence or absence of the metabolic disorder.

Further, the invention provides a method for detecting a metabolic disorder in an individual that involves (a) separating a sample into two sample portions, the sample comprising: (i) one or more metabolically indicative enzymes and (ii) one or more metabolic analytes; (b) contacting each sample portion with one or more substrates for the one or more enzymes to produce two reaction admixtures, under conditions wherein at least one of the enzymes in each sample portion is capable of acting on a corresponding substrate to generate at least one product, and wherein one or more protease inhibitors are present in at least one of the reaction admixtures; (c) contacting each reaction admixture with a reagent that inhibits the ability of the one or more enzymes to act on a corresponding substrate, wherein the reagent can be the same or different for each reaction admixture, and wherein the one or more metabolic analytes and at least one product are soluble in the reagent or reagents and (d) combining the two reaction admixtures to produce a test sample, and (e) determining the presence or amount of the one or more metabolic analytes and the at least one product contained in the test sample using mass spectrometry, wherein a determined presence or amount of the one or more metabolic analytes and the at least one product correlates with presence or absence of the metabolic disorder.

Yet another method for detecting a metabolic disorder in an individual provided by the invention involves (a) separating a sample into two sample portions, the sample comprising: (i) one or more metabolically indicative enzymes and (ii) one or more metabolic analytes; (b) contacting each sample portion with individual vessels, each vessel containing one or more substrates for the one or more enzymes in dried form, (c) contacting each vessel with a solution to produce two reaction admixtures, under conditions wherein at least one of the enzymes in each sample portion is capable of acting on a corresponding substrate to generate at least one product, and wherein one or more protease inhibitors are present in at least one of said reaction admixtures; (d) contacting each reaction admixture with a reagent that inhibits the ability of the one or more enzymes to act on a corresponding substrate, wherein the reagent can be the same or different for each reaction admixture, and wherein the one or more metabolic analytes and the at least one product are soluble in the reagent or reagents and (e) combining the two reaction admixtures to produce a test sample, and (f) determining the presence or amount of the one or more metabolic analytes and the at least one product contained in the test sample using mass spectrometry, wherein a determined presence or amount of the one or more metabolic analytes and the at least one product correlates with presence or absence of the metabolic disorder.

BRIEF DESCRIPTION OF THE DRAWINGS

FIG. 1 shows detection of biotinidase activity using a method of the invention in comparison to that using standard fluorometric methods.

DETAILED DESCRIPTION

This invention relates to the discovery of metabolic disorder diagnostic tests that allow detection of at least two relevant markers simultaneously and from a single sample. In particular, the inventor has discovered that one sample can be used to simultaneously detect a metabolic analyte, as well as activity of a metabolic enzyme, using mass spectrometry.

The present invention involves detecting at least two markers or indicia of one or more metabolic disorders from a single sample. At least one index corresponds to the activity of a metabolically indicative enzyme in the sample, and at least one index corresponds to the presence or amount of a metabolic analyte endogenously contained in the sample. Previous clinical methods for genetic screening using mass spectrometry detected only metabolic analytes in a single sample. In particular, Chace (U.S. Pat. No. 6,258,605 and U.S. Pat. No. 6,455,321) describes preparing a patient sample (dried blood spot) by extraction in methanol prior to analysis. Under such conditions, enzymes are inactive such that measuring enzyme activity is unfeasible, moreover, uncontemplated.

Well-known methods for determining enzymatic activity do not include detection of metabolic analytes but instead measure a tag on the enzymatic product, such as a fluorescent tag. Modes of detection for tagged products cannot simultaneously detect metabolic analytes present in a patient sample. Another disadvantage of fluorimetric methods with respect to enzymatic assays is that artificial substrates tagged with a fluorescent group are different enough from their natural counterparts that enzyme activity toward such substrates is inherently reduced and thus sensitivity of the assays is reduced. The methods of the invention advantageously can involve detection of metabolically indicative enzyme activity toward natural substrate.

As described in Example I, the activity of metabolically indicative enzyme biotinidase, as well as the concentration of alpha amino acids and carnitines, were simultaneously determined from a single sample. As is shown in FIG. 1, in spite of its multiplex character, the sensitivity of the method for detecting biotinidase (FIG. 1) is comparable to a well-known fluorimetric enzyme assay method. The letter A,B,C,D,E, and F shown in Tables 6 and 7, a method of the invention has samples, "calibrators", Similarly, as shown in Tables 6 and 7, a method of the invention has sensitivity comparable to well-known mass spectrometry methods that measure analytes without regard for enzyme activities. Based on this discovery of simultaneous detection of metabolic analytes and enzyme activity from a single sample, the invention provides methods for detecting metabolic disorders. As is described in Example 2, the accuracy of amino acid amounts detected using a method of the invention can be increased by including one or more protease inhibitors in the selected assay format.

Detecting of a metabolic disorder can be used in diagnosing or predicting susceptibility to a metabolic disorder because biochemical indicators examined using the methods of the invention are indicative of a metabolic disorder, whether or not physiologic or behavioral symptoms of the disorder have become apparent.

The methods of the invention also are useful for monitoring the metabolism of an individual, such as one undergoing treatment for a metabolic disorder. As a non-limiting example, the methods can be used for determining therapeutic efficacy of a particular treatment. Based on this determination, the individual can be offered additional or alternative therapeutic options. The methods of the invention also can be useful for assessing patient compliance with a particular treatment modality, such as dietary restriction. Therefore, the invention is applicable to screening, diagnosis, prognosis, monitoring therapy and compliance, and any other application in which determining the presence or amount of one or more metabolic analytes and at least one metabolically indicative enzyme activity is useful.

The methods of the invention involve detecting two or more analytes and metabolically indicative enzyme activities simultaneously. By providing a multiplexed format, the invention advantageously reduces technical performance errors because the number of manipulations is fewer than tests performed separately. Moreover, assay costs associated with simultaneous detection of multiple analytes and enzyme activitites is lower than those associated with individual tests because fewer materials (assay vessels, liquid transfer materials, and the like) are used and less operator time is required.

As used herein, the term "metabolic disorder" means any abnormal condition in the body that causes loss of metabolic control of the body's steady state. Metabolism is the physiological and biochemical process by which food is converted in the body to forms that provide energy for bodily activities. Metabolism includes creation of specific molecules that the body uses for its myriad activities. Such molecules include hormones, neurotransmitters, proteins such as enzymes, and membrane constituents. Metabolism also includes degradation processes that enable cells to excrete waste products. Exemplary metabolic processes include processes for absorption and modification of vitamins and minerals; for degrading molecules to provide energy or to be excreted; processes for making acetyl-coenzyme A, nonessential amino acids, cholesterol, long-chain fatty acids, prostaglandins, complex lipids and proteins; and for neutralizing toxins. Therefore, a metabolic disorder is a condition that interferes with normal creation or destruction of biological molecules that regulate health. A metabolic disorder arising early in life and resulting from genetic inheritance is generally referred to as an "inborn error of metabolism", whereas a metabolic disorder that arises as a result of disease or lifestyle is generally referred to as an "acquired metabolic disorder", although genetic predisposition generally exists.

Elevated amino acids, free carnitine and acylcarnitine levels are examples of metabolites that can be indicative of one or more of several metabolic disorders. Free carnitine and acylcarnitines are markers for disorders that are classified as fatty acid oxidation (FAO) disorders and organic aciduria disorders (OAD). Similarly, amino acids are used as markers for several metabolic disorders collectively known as amino acidopathies.

In Fatty Acid Oxidation (FAO) Disorders disorders, enzymes necessary for fatty acid breakdown are unavailable or have reduced activity. Breakdown, or oxidation, of fatty acids is necessary for energy production when glucose levels, the body's main source of energy, are low. Without this energy supply some individuals may have recurring incidences of low blood sugar levels. In cases of fasting, often caused by illnesses such as ear infections or flu, there may be metabolic crisis. Affected individuals may show vomiting, diarrhea, lethargy, seizures and coma. Failure to diagnose FAO disorders may result in excessive fat buildup in the liver, heart and kidneys. This buildup can cause a variety of symptoms, ranging from hepatic failure, encephalopathy, and heart and eye complications to general problems with muscle development. Many of these clinical symptoms can lead to death. Many deaths due to FAO disorders have been misdiagnosed as SIDS or Reye's Syndrome.

In Organic Aciduria (OA) Disorders, the metabolic pathways of organic acids are disrupted and thus accumulation of the acids in blood and urine alters the acid-base balance of the body. Resulting modifications or adaptations to intermediary metabolic pathways may cause numerous clinical symptoms, including metabolic acidosis, ketosis, hyperammonemia, failure to thrive, sepsis or coma.

In disorders of amino acid metabolism (amino acidopathies), enzymes necessary for the metabolism of certain amino acids are unavailable or have reduced activity. As a result, the concentration of the affected amino acids and alternate metabolites increases in the infant's body. These excesses can have deleterious effects on the infant's health including death. Some commonly studied amino acidopathies are:

Phenylketonuria (PKU) is a disorder of aromatic amino acid metabolism in which phenylalanine cannot be converted to tyrosine. If untreated, PKU leads to various degrees of mental retardation. Hyperphenylalaninemia leads to mental retardation and muscular rigidity. Homocystinuria leads to vascular occlusive disease, osteoporosis, accumulation of homocystine and methionine, and variable developmental delays. Maple Syrup Urine Disease (MSUD) is caused by a disorder of branched-chain amino acid metabolism resulting in elevated levels of leucine, isoleucine and valine in the blood. If untreated, lethargy progressive to coma, developmental delay, and convulsions will develop. Tyrosinemia type I (hereditary tyrosinemia), leads to acute hepatic failure or chronic cirrhosis and hepatocellular carcinoma. Citrullinemia leads to convulsions, anorexia, vomiting and lethargy, followed rapidly by potentially lethal coma.

As used herein, the term "metabolically indicative" when used in reference to an enzyme means that the amount or activity of the enzyme is altered as a result of a metabolic disorder in an individual. Therefore, the amount or activity of a metabolically indicative enzyme can be increased or decreased in an individual having a metabolic disorder in comparison to an individual free of the metabolic disorder. Although the activity of a metabolically indicative enzyme can be altered in an individual having a metabolic disorder, it is understood that the individual can be free of, or can have outward signs or symptoms of, the disorder.

As used herein, the term "metabolic analyte" means a substance that is altered in amount, activity, or physical characteristic in the body of an individual experiencing a metabolic disorder in comparison to an individual not experiencing a metabolic disorder. Exemplary metabolic analytes include an amino acid, fatty acid and organic acid, and other small biological molecules, as well as a macromolecule such as a nucleic acid, polypeptide or carbohydrate, and the like.

The invention provides methods for detecting a metabolic disorder in an individual. One method involves (a) contacting a sample containing (i) one or more metabolically indicative enzymes and (ii) one or more metabolic analytes, with one or more substrates for the one or more enzymes to produce a reaction admixture, under conditions wherein at least one of the enzymes is capable of acting on a corresponding substrate to generate at least one product, and wherein one or more protease inhibitors are present; (b) contacting the reaction admixture with a reagent that inhibits the ability of the one or more enzymes to act on a corresponding substrate, wherein the one or more metabolic analytes and the at least one product are soluble in the reagent; to produce a test sample and (c) determining the presence or amount of the one or more metabolic analytes and the at least one product contained in the test sample using mass spectrometry wherein a determined presence or amount of the one or more metabolic analytes and the at least one product correlates with presence or absence of the metabolic disorder.

The invention provides another method for detecting a metabolic disorder. The method involves (a) contacting a vessel containing one or more substrates in dried form with a sample from the individual, the sample containing (i) one or more metabolically indicative enzymes and (ii) one or more metabolic analytes, in aqueous solution under conditions wherein at least one of the enzymes is capable of acting on a corresponding substrate to generate at least one product, and wherein one or more protease inhibitors are present; (b) adding a reagent that inhibits the ability of the one or more enzymes to act on a corresponding substrate, wherein the one or more metabolic analytes and at least one product are soluble in the reagent; (c) determining the presence or amount of the one or more metabolic analytes and the at least one product in the resultant mixture using mass spectrometry wherein a determined presence or amount of the one or more metabolic analytes and the at least one product correlates with presence or absence of the metabolic disorder.

The invention provides a further method for detecting a metabolic disorder in an individual. The method involves (a) contacting a sample comprising: (i) one or more metabolically indicative enzymes and (ii) one or more metabolic analytes, with one or more substrates for the one or more enzymes to produce a reaction admixture, under conditions wherein at least one of the enzymes is capable of acting on a corresponding substrate to generate at least one product, and wherein one or more protease inhibitors are present; (b) contacting the reaction admixture with a reagent that inhibits the ability of the one or more enzymes to act on a corresponding substrate, wherein the one or more metabolic analytes and the at least one product are soluble in the reagent, to produce a test sample; (c) contacting the reaction admixture with one or more reference products and one or more reference analytes, and (d) determining the presence or amount of the one or more metabolic analytes and the at least one product contained in the test sample, with respect to the one or more reference products and one or more reference analytes, using mass spectrometry, wherein a determined presence or amount of the one or more metabolic analytes and the at least one product correlates with presence or absence of the metabolic disorder.

Another method for detecting a metabolic disorder in an individual involves (a) contacting a vessel containing one or more substrates in dried form with a sample from the individual, the sample containing (i) one or more metabolically indicative enzymes and (ii) one or more metabolic analytes, (b) contacting the vessel with a solution to generate conditions wherein at least one of the enzymes is capable of acting on a corresponding substrate to generate at least one product, and wherein one or more protease inhibitors are present; (c) adding a reagent that inhibits the ability of the one or more enzymes to act on a corresponding substrate, wherein the one or more metabolic analytes and at least one product are soluble in the reagent; (d) determining the presence or amount of the one or more metabolic analytes and the at least one product in the resultant mixture using mass spectrometry, wherein a determined presence or amount of the one or more metabolic analytes and the at least one product correlates with presence or absence of the metabolic disorder.

Further, the invention provides a method for detecting a metabolic disorder in an individual that involves (a) separating a sample into two sample portions, the sample comprising: (i) one or more metabolically indicative enzymes and (ii) one or more metabolic analytes; (b) contacting each sample portion with one or more substrates for the one or more enzymes to produce two reaction admixtures, under conditions wherein at least one of the enzymes in each sample portion is capable of acting on a corresponding substrate to generate at least one product, and wherein one or more protease inhibitors are present in at least one reaction admixture; (c) contacting each reaction admixture with a reagent that inhibits the ability of the one or more enzymes to act on a corresponding substrate, wherein the reagent can be the same or different for each reaction admixture, and wherein the one or more metabolic analytes and the at least one product are soluble in the reagent or reagents and (d) combining the two reaction admixtures to produce a test sample, and (e) determining the presence or amount of the one or more metabolic analytes and the at least one product contained in the test sample using mass spectrometry, wherein a determined presence or amount of the one or more metabolic analytes and the at least one product correlates with presence or absence of the metabolic disorder.

Yet another method for detecting a metabolic disorder in an individual provided by the invention involves (a) separating a sample into two sample portions, the sample comprising: (i) one or more metabolically indicative enzymes and (ii) one or more metabolic analytes; (b) contacting each sample portion with individual vessels, each vessel containing one or more substrates for the one or more enzymes in dried form, (c) contacting each vessel with a solution to produce two reaction admixtures, under conditions wherein at least one of the enzymes in each sample portion is capable of acting on a corresponding substrate to generate at least one product, and wherein one or more protease inhibitors are present in at least one of said reaction admixtures; (d) contacting each reaction admixture with a reagent that inhibits the ability of the one or more enzymes to act on a corresponding substrate, wherein the reagent can be the same or different for each reaction admixture, and wherein the one or more metabolic analytes and the at least one product are soluble in the reagent or reagents and (e) combining the two reaction admixtures to produce a test sample, and (f) determining the presence or amount of the one or more metabolic analytes and the at least one product contained in the test sample using mass spectrometry, wherein a determined presence or amount of the one or more metabolic analytes and the at least one product correlates with presence or absence of the metabolic disorder.

In any of the above methods for detecting a metabolic disorder, one or more reference products and/or reference analytes can be added to a test sample prior to mass spectrometry. Similarly, one or more reference substrates can be added to a reaction admixture or solution before an enzymatic reaction is allowed to proceed. Such additions can be useful when the methods are carried out in a quantitative format, as is described in more detail herein below.

The methods of the invention can be carried out in a variety of formats. As an example of a typical procedure, a sample from a normal individual or one suspected of having a metabolic disorder is placed in a vessel. The type of the sample (for example, whole blood, serum, tissue) is chosen based on the particular metabolic disorder, and any sample pre-treatment to release enzymes is performed based on the sample type. An enzyme that correlates with the test subject metabolic disorder is known, as is the enzyme substrate. At least one metabolic analyte known to correlate with the metabolic disorder, or a related or different metabolic disorder, is also known.

To the sample is added an aqueous solution containing a substrate for the enzyme indicative of the metabolic disease. The aqueous solution can contain a protease inhibitor, if desired, to produce a reaction admixture containing one or more protease inhibitors. The enzymatic reaction is allowed to proceed for a time period sufficient for the enzyme to produce a detectable or desired amount of product. The reaction is then stopped by adding a stop reagent that includes a reference analyte to be detected. The reagent denatures the enzyme, but maintains the product and reference form of metabolic analyte in solution (reference analyte). The sample is subjected to tandem mass spectrometry to detect the product, metabolic analyte, and reference analyte. The amount of metabolic analyte is determined based on the reference analyte, and the presence of the product is detected.

As another example, a sample from a normal individual or one suspected of having a metabolic disorder is added to a vessel containing the metabolically indicative enzyme substrate. If the sample is contained in a suitable solution, the enzymatic reaction is allowed to proceed. If the sample is in dried form, such as on membrane or paper, a suitable solution is applied to the sample when in the vessel. The suitable solution can contain a protease inhibitor, if desired, to produce a reaction admixture containing one or more protease inhibitors. After a time period sufficient to solubilize the enzyme or allow enzyme to be released from the material on which it is dried (if present), the enzymatic reaction is allowed to proceed. As above, the enzymatic reaction is allowed to proceed for a time period sufficient for the enzyme to produce a detectable or desired amount of product. The reaction is then stopped by adding a stop reagent that includes a reference analyte and a reference product. The amounts of metabolic analyte and enzymatic product are determined based on the reference analyte and product.

As a further example of a procedure for performing a method of the invention, after addition of the stop reagent, the test sample can be processed to separate soluble from insoluble material. Separation can be performed, for example, by centrifugation, filtration and the like. The resultant clarified test sample can then be subjected to mass spectrometry. Another optional step is to add a detergent or other solubilizing agent to the test sample, for example in the case that the reaction admixture and reagent are immiscible.

Although not required, the test sample can be derivatized prior to mass spectrometry to enhance detection of the amount of metabolic analyte, enzymatic product and/or reference substance. An exemplary well-known derivatization method is reaction of sample with acid and butanol.

A method of the invention can be used to simultaneously determine presence or amount of one or more metabolic analytes and at least one enzymatic product. As such, the methods are applicable to simultaneously determining presence or amount of two or more metabolic analytes and at least one enzymatic product, three or more metabolic analytes and at least one enzymatic product, four or more metabolic analytes and at least one enzymatic product, including at least five metabolic analytes, at least five metabolic analytes, at least ten metabolic analytes and at least twenty metabolic analytes, together with a at least one enzymatic product. Similarly, the methods are applicable to simultaneously determining presence of amount of one or more metabolic analytes and two or more enzymatic products, one or more metabolic analytes and three or more enzymatic products, one or more metabolic analytes and four or more enzymatic products, one or more metabolic analytes and five more enzymatic products, as well as one or more metabolic analytes and more than five enzymatic products.

The methods of the invention involve detecting a metabolic disorder by testing a "sample". As used herein, the term "sample" means any biological fluid, cell, tissue, or fraction thereof, that includes one or more enzymes having an endogenous enzyme indicative of a metabolic state, and one or more endogenous metabolic analytes. A sample can be, for example, a specimen obtained from an individual or can be derived from such a specimen. For example, a sample can be a tissue section obtained by biopsy, or cells that are placed in or adapted to tissue culture. Exemplary samples therefore include cultured fibroblasts, cultured amnionic fluid cells, and chorionic villus sample. A sample can also be a biological fluid specimen such as urine, blood, plasma, serum, saliva, semen, sputum, cerebral spinal fluid, tears, mucus, and the like. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from an individual such as a combination of a tissue and fluid sample, and the like.

For use in the methods of the invention, a sample contains one or more metabolically indicative enzymes and one or more endogenous metabolic analytes. To allow enzyme activity to occur in solution while practicing the methods of the invention, the sample can be suitably processed to release metabolically indicative enzyme(s) and/or endogenous metabolic analytes into solution. Well known methods for releasing or solubilizing enzymes in samples containing cells include treatment with detergent, freeze/thaw treatment, drying and rehydrating, and the like.

The origin of a sample used in a method of the invention will depend upon the metabolically indicative enzyme(s) and metabolic analyte(s) to be detected. The body fluids and tissues in which metabolically indicative enzymes and metabolic analytes are contained are well know to those skilled in the art. As non-limiting examples, a whole blood sample can be used when biotinidase is the metabolically indicative enzyme; a liver biopsy can be used when carbamylphosphate synthetase is the metabolically indicative enzyme; urine can be used when branched-chain ketoacid dehydrogenase is the metabolically indicative enzyme and a skin biopsy can be used when alpha-L-fucosidase is the metabolically indicative enzyme.

Methods for obtaining samples that preserve the activity or integrity of molecules in the sample are well known to those skilled in the art. Such methods include the use of appropriate buffers and/or inhibitors, including nuclease, protease and phosphatase inhibitors, that preserve or minimize changes in the molecules in the sample. Such inhibitors include, for example, chelators such as ethylenediamne tetraacetic acid (EDTA), ethylene glycol bis(P-aminoethylether)N,N,N1,NI-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances. As such, a mixture used in a method of the invention, such as a "reaction admixture" can contain one or more inhibitors, such as one or more protease inhibitors. Example 2 describes results of experiments in which protease inhibitors were included in a reaction admixture.

Various methods to fractionate a fluid sample or cell extract are well known to those skilled in the art, including subcellular fractionation or chromatographic techniques such as ion exchange, hydrophobic and reverse phase, size exclusion, affinity, hydrophobic charge-induction chromatography, and the like (Ausubel et al. supra, 1999; Scopes, Protein Purification: Principles and Practice, third edition, Springer-Verlag, New York (1993); Burton and Harding, J. Chromatoqr. A 814:71-81 (1998)). As an example, a serum sample from an individual containing leukocytes can be fractionated to isolate leukocytes, if desired, or subfractionated, for example, into macrophages, T cells, B cells, granuolocytes, monocytes, neutrophils, eosinophils, basophils, mast cells, and the like.

For use in a method of the invention, a sample can be in a variety of physical states. For example, a sample can be a liquid or solid, can be dissolved or suspended in a liquid, can be in an emulsion or gel, and can be absorbed onto a material. As a non-limited example, a sample can be a liquid blood sample, liquid serum sample, liquid white blood cell sample, dried blood, serum, or white cell sample, or such a sample absorbed onto a paper or polymer substrate. Example 1 describes use of a dried blood sample in a method of the invention.

A sample used in a method of the invention can be separated prior to use. Separation can be desirable if particular metabolically indicative enzymatic activities present in the sample require distinct assay conditions, or if particular metabolic analytes endogenously present in the sample are soluble in different solution environments. Separation also can be desirable to reduce the presence of substances that interfere with detection of a metabolically indicative enzyme or metabolic analyte in a sample, and to retain that interfering portion of the sample in order to detect one or more distinct metabolically indicative enzymes or metabolic analytes in the portion.

Individuals of all ages can be affected by a metabolic disorder. Therefore, a sample used in a method of the invention can be obtained from an individual of any age, including a neonate, newborn, baby, child, and adult. Exemplary metabolic disorders that can be characterized by adult onset include Schindler disease (lysosomal enzyme alpha-N-acetylgalactosamimidase deficiency), urea cycle disorders and sphingolipidoses. The methods of the invention are applicable to human and non-human individuals. As such, the methods can be used on a sample obtained, for example, from any veterinary or research subject for which a metabolically indicative enzyme and endogenous metabolic analyte are known.

Exemplary non-human animals include a horse, dog, cat, rabbit, rat, mouse, fish, turtle and lizard. The methods of the invention also are applicable to lower organisms, such as yeast, archebacteria and bacteria, and plants, so long as a sample containing an endogenous metabolically indicative enzyme and endogenous metabolic analyte can be obtained.

The methods of the invention involve detecting the enzymatic product of at least one "metabolically indicative enzyme". Any metabolically indicative enzyme can be assayed using the methods of the invention, so long as a substrate is known for the enzyme, which substrate is soluble in a selected "reagent," and which substrate can be modified to a form distinctly detectable by mass spectrometry, if desired, for use as an internal standard. Metabolically indicative enzymes are represented in every enzyme class, including oxidoreductases, hydrolases, lyases, transferases, ligases and isomerases. As a non-limiting example, well-known metabolically indicative enzymes and their associated metabolic disorders are shown below in Table 1. A specific example of a metabolically indicative enzyme is biotinidase.

TABLE 1

| Metabolic disorder | Metabolically indicative enzyme | Exemplary metabolic analyte |
|---|---|---|
| 3-methylglutaconic aciduria | 3-methylglutaconic hydratase | 3-methylglutaconic acid |
| Smith-Lemli-Opitz Syndrome | | 7-dehydrocholestrerol |
| 4-hydroxylbutyric aciduria | Succinic semialdehyde dehydrogenase | |
| Adenylosuccinate lyase deficiency | Adenylosuccinate lyase | succinylAICA riboside and succinyladenosine |
| Beta-Ketothiolase | 3-oxoacid CoA transferase | |

TABLE 1-continued

| Metabolic disorder | Metabolically indicative enzyme | Exemplary metabolic analyte |
|---|---|---|
| Deficiency | and beta-ketothiolase. | |
| Biotinidase deficiency | Biotinidase | Biotin |
| Carbamylphosphate synthetase deficiency | Carbamylphosphate synthetase | |
| Duarte Galactosemia | Gal-1-P-uridyltransferase | Gal-1-P |
| Ehlers-Danlos Syndrome, Type VI | Lysyl hydroxylase | pyridinoline (Pyr), and deoxypyridinoline, (Dpyr), and their ratio |
| Fucosidosis | alpha-L-fucosidase | |
| Guanidinoacetate Methyltransferase Deficiency | Guanidinoacetate methyltransferase | Guanidinoacetate |
| Krabbe Disease | Beta-Galactocerebrosidase | |
| Long Chain Acyl-CoA Dehydrogenase Deficiency | Acyl-CoA Dehydrogenases: Short-, Medium-, and Long Chain | |
| Maple Syrup Urine Disease | Branched-Chain Ketoacid Dehydrogenase | branched chain amino acids (valine, isoleucine and leucine) |
| Methyltetrahydrofolate Reductase Deficiency | Methyltetrahydrofolate Reductase | |
| Phenylketonurea | phenylalanine hydroxylase | Biopterin, Pteridine, Phenylalanine |
| Tay-Sachs Disease | Beta-N-Acetylglucosaminidase, Hexosaminidase (Beta-Hexosaminidase-A) | Gangliosides |
| Urea Cycle Disorder | Argininase, Argininosuccinate Lyase, Carbamyl Phosphate Synthetase | Orotic acid |
| Zellweger Syndrome | Dihydroxyacetonephosphate acyltransferase, Phytanic Acid Oxidase | Pipecolic Acid, Very Long Chain Fatty Acids |
| Classic galactosemia | Galactose-1-phosphate uridyl transferase (GALT) | |
| Galactosemia | Galactokinase | |
| Galactosemia | Uridine diphosphate galactose-4-epimirase | |
| G6PD deficiency | Glucose-6-phosphate dehydrogenase (G6PD) | |
| Sialidosis type II | Neuraminidase | |
| Hurler disease | α-Iduronidase | |
| Hunter diease | Iduronate sulfatase | |
| Sanfilipo disease type A (MPS IIIA) | Heparan sulphamidase | |
| Sanfilipo disease type B (MPS IIIB) | α-N-acetyl glucosaminidase | |
| Sanfilipo disease type C (MPS IIIC) | Glucosamine N-acetyl transferase | |
| Morquio disease type A (MPS IVA) | N-acetyl galactosamine-6-sulphatase | |
| Morquio disease type B (MPS IVB) | β-Galactosidase | |
| Maroteaux-Lamy disease (MPS VI) | Arylsulphatase B | |
| Sly disease (MPS VII) | β-Glucoronidase | |
| α-Mannosidosis | α-Mannosidase | |
| β-Mannosidosis | β-Mannosidase | |
| α-Fucosidosis | α-Fucosidase | |
| Sialidosis | α-N-acetylneuraminidase | |
| Galactosialidosis | α-N-acetylneuraminidase, β-Galactosidase | |
| Aspartylglucosaminuria | Aspartylglucosaminidase | |
| Schidler disease | α-N-acetylgalactosaminidase, | |
| Pompe disease | α-Glucosidase | |
| Tay-Sachs | α-Hexosaminidase | |
| Sandhoff disease | α-Hexosaminidase | |
| GM-1 gangliosidosis | β-Galactosidase | |
| Gaucher disease | β-Glucosidase, Chitotriosidase | |
| Krabbe disease | Galactocerebrosidase | |
| Metachromatic leucodystrophy | Arylsulphatase A | |

TABLE 1-continued

| Metabolic disorder | Metabolically indicative enzyme | Exemplary metabolic analyte |
|---|---|---|
| Fabry disease | α-Galactosidase A | |
| Farber disease | Ceramidase | |
| Niemann-Pick disease | Sphingomyelinase | |

Substrates for metabolically indicative enzymes are well known to those skilled in the art. As used herein, the term "substrate" means a molecule or complex acted upon by a metabolically indicative enzyme. In particular, a substrate has a physiological affinity for and must be able to be acted upon by a corresponding enzyme. A substrate useful in the methods of the invention can be native or modified. Modified substrates useful in the invention have a mass different from the native substrate and retain the ability to be acted upon by the corresponding enzyme. A variety of chemical modification reactions useful for increasing the mass of a substrate are well known to those skilled in the art. Exemplary modifications suitable for substrates include isotopic labeling and any chemical modification that alters the mass or mass-to-charge ratio of the substrate. Once a substrate is modified, activity can be confirmed using routine methods, such as comparison of enzyme activity using native substrate vs. modified substrate, or by quantitation of the product via internal standardization using one or more reference products of known concentration. As a non-limiting example, when the metabolically indicative enzyme is biotinidase, a substrate can be native biocytin or modified biocytin.

As used herein, the term "product" when used in reference to enzymatic activity means a molecular entity that is produced as a result of enzyme acting on substrate. Therefore, the presence or amount of a product in a sample correlates with the presence or amount of enzymatic activity in the sample. As such, an amount of product determined using a method of the invention can be expressed as a level of enzymatic activity using routine calculations, if desired, for example, when assessing differences between test sample and reference level enzymatic activity.

The methods of the invention involve use of a reagent that inhibits the ability of one or more metabolically indicative enzymes to act on a corresponding substrate, As used herein, the term "inhibit" means to reduce or block enzyme activity such that product formation is undetectable or insignificant.

As used herein, a "reagent" for use in the methods of the invention is or contains a chemical agent that specifically or non-specifically inhibits the ability of a metabolically indicative enzyme to act on a corresponding substrate, and does not substantially interfere with mass spectrometry analysis. Exemplary non-specific reagents that inhibit enzymatic reactions are chaotropes, which are chemical agents that denature proteins, and solutions containing chaotropes. Non-limiting examples of chaotropes are alcohols, such as methanol, ethanol and isobutyl alcohol; urea and guanidine salts. Exemplary specific reagents that inhibit enzymatic reactions include enzyme inhibitors effective for a selected enzyme. A large number of enzyme inhibitors are widely available and well-known to those skilled in the art. A reagent for use in the methods of the invention can be selected based on, for example, suitability for inhibiting activity of metabolically indicative enzyme(s), and ability to maintain solubility of metabolic analyte(s) and enzymatic product(s). A selected reagent can be selected to have a minimal number of components in order to minimize background for mass spectrometry. A selected reagent can be miscible or immiscible with a particular reaction admixture or solution, with rapid mixing being one method for ensuring that enzymatic reaction is inhibited. Examples of reagents useful in the invention include organic solvents and solutions thereof, organic acids and solutions thereof, alcohols and solutions thereof, reagents that are non-polar relative to the reaction admixture or solution, and reagents that have a pH distinct from the reaction admixture or solution, the pH creating an unsuitable environment for enzymatic activity, and the like. Non-limiting specific reagents include methanol and solutions thereof; trifluoroacetic acid and solutions thereof; and acetonitrile and solutions thereof. Those skilled in the art of mass spectrometry will be able to identify reagents that do not interfere with mass spectrometry determinations.

The ability of a selected regent to inhibit an enzymatic reaction can be determined by routine methods. For example, the effectiveness of a candidate "reagent" can be tested by adding the reagent or a known inhibitor of the enzyme to an enzymatic reaction in progress. The amount of enzymatic activity under each condition can then be compared to confirm if a selected reagent is suitable for use in the invention methods.

The methods of the invention involve detecting at least one "metabolic Analyte". A variety of metabolic analytes can be detected using the methods of the invention, so long as the analyte is soluble in a selected reagent, has a known mass, and can be modified, if desired, for use as an internal standard. Metabolic analytes associated with particular metabolic disorders are well known to those skilled in the art. As non-limiting examples, well-known metabolic analytes and their associated metabolic disorders are shown above in Table 1. Amino acid and carnitine metabolic analytes are shown in Table 2, and can correspond with common metabolic disorders shown in Table 3. Amino acid disorders and corresponding amino acid metabolic analytes are also shown in Table 4. Fatty acid disorders and corresponding fatty acid metabolic analytes are shown in Table 5; additional fatty acid disorders shown in Table 3.

TABLE 2

| ANALYTE NAME | ABBREVIATION |
|---|---|
| Amino Acids | |
| Alanine | Ala |
| Arginine | Arg |
| Citruline | Cit |
| Glycine | Gly |
| Leucine | Leu |
| Methionine | Met |
| Ornithine | Orn |
| 5-Oxoproline | 5-Oxo Pro |
| Phenylalanine | Phe |
| Tyrosine | Tyr |
| Valine | Val |
| Proline | Pro |

TABLE 2-continued

| ANALYTE NAME | ABBREVIATION |
|---|---|
| Carnitines | |
| Free carnitine | C0 |
| Acetylcarnitine | C2 |
| Propionylcarnitine | C3 |
| Malonylcarnitine | C3DC |
| Butyrylcarnitine | C4 |
| 3-Hydroxy-butyrylcarnitine | C4OH |
| Isovalerylcarnitine | C5 |
| Tiglylcarnitine | C5:1 |
| Glutarylcarnitine | C5DC |
| 3-Hydroxy-isovalerylcarnitine | C5OH |
| Hexanoylcarnitine | C6 |
| Adipylcarnitine | C6DC |
| Octanoylcarnitine | C8 |
| Octenoylcarnitine | C8:1 |
| Decanoylcarnitine | C10 |
| Decenoylcarnitine | C10:1 |
| Decadienoylcarnitine | C10:2 |
| Dodecanoylcarnitine | C12 |
| Dodecenoylcarnitine | C12:1 |
| Tetradecanoylcarnitine (Myristoylcarnitine) | C14 |
| Tetradecenoylcarnitine | C14:1 |
| Tetradecadienoylcarnitine | C14:2 |
| 3-Hydroxy-tetradecanoylcarnitine | C14OH |
| Hexadecanoylcarnitine (palmitoylcarnitine) | C16 |
| Hexadecenoylcarnitine | C16:1 |
| 3-Hydroxy-hexadecanoylcarnitine | C16OH |
| 3-Hydroxy-hexadecenoylcarnitine | C16:1OH |
| Octadecanoylcarnitine (Stearoylcarnitine) | C18 |
| Octadecenoylcarnitine (Oleylcarnitine) | C18:1 |
| Octadecadienoylcarnitine (Linoleylcarnitine) | C18:2 |
| 3-Hydroxy-octadecanoylcarnitine | C18OH |
| 3-Hydroxy-octadecenoylcarnitine | C18:1OH |

TABLE 3

Amino Acid Disorders

| | |
|---|---|
| ARGD | Argininemia |
| ASA, ASL, ALD | Argininosuccinic aciduria (Argininosuccinate lyase deficiency, Argininosuccinase deficiency) |
| ASD, ASS | Citrullinemia (Argininosuccinic acid synthetase deficiency, Argininosuccinate synthetase deficiency) |
| HCU, HCYS | Homocystinuria (Cystathione synthase deficiency) |
| Hmet | Hypermethioninemia |
| HHH | Hyperornithinemia, Hyperammonemia, Hyperhomocitrullinuria syndrome (Ornithine translocase deficiency) |
| PRO | Hyperprolinemia |
| MSUD, BCKA | Maple Syrup Urine Disease (Branched chain ketoaciduria) |
| NKG, NKHI | Nonketotic hyperglycinemia |
| PKU | Phenylketonuria |
| PYP/PIP | Pyroglutamic/pipecolic acidemia |
| | Tyrosenemia, Type I |
| | Tyrosenemia, Type II |
| | 5-oxoprolinuria |
| | (Pyroglutamic aciduria) |

Fatty Acid and Organic Acid Disorders

| | |
|---|---|
| 2-MBCD | 2-methylbutyryl CoA dehydrogenase deficiency |
| | 2,4-Dienoyl-CoA reductase deficiency |
| HMG | 3-hydroxy-3-methylglutaryl CoA lyase deficiency (hydroxymethylglutaric acidemia) |
| 3MCC, 3-MMC | 3-methylcrotonyl CoA carboxylase deficiency (3-methylcrotonylglycinemia) |
| CPT I | Carnitine palmitoyltransferase, type I deficiency |
| CPT II | Carnitine palmitoyltransferase, type II deficiency |
| CTD | Carnitine transporter defect |
| CATR, CACT | Carnitine/acylcarnitine translocase defect |

TABLE 3-continued

| | |
|---|---|
| EMA | Ethylmalonic acidemia |
| GA I | Glutaric acidemia, type I (Glutaryl CoA dehydrogenase deficiency) |
| IBCD | Isobutyryl CoA dehydrogenase deficiency |
| IVA | Isovaleric acidemia |
| LCAD | Long-chain acyl-CoA dehydrogenase deficiency |
| LCHAD | Long-chain hydroxyacyl-CoA dehydrogenase deficiency |
| MA | Malonic aciduria |
| MCAD | Medium-chain acyl-CoA dehydrogenase deficiency |
| MMA | Methylmalonic acedemia |
| BKT | Mitocondrial acetoacetyl CoA thiolase deficiency (Beta-Ketothiolase deficiency) |
| MADD, GA II | Multiple acyl-CoA dehydrogenase deficiency (Glutaric acidemia, type II) |
| MCD | Multiple Co-A carboxylase deficiency (Holocarboxylase synthetase deficiency) |
| PA, PPA | Propionic acidemia |
| SCAD | Short-chain acyl-CoA dehydrogenase deficiency |
| SCHAD | Short-chain hydroxyacyl-CoA dhydrogenase deficiency |
| TFP | Trifunctional protein deficiency |
| VLCAD | Very-long-chain acyl-CoA dehydrogenase deficiency |

TABLE 4

Aminoacidopathies

Phenylketonuria

Phe[2,4,6]
Phe, Phe/Tyr[7]
Phe, Tyr[1,5]

Maple syrup urine disease

Leu + Ile[1]
Leu + Ile, Val[2,4,6]
Leu, Val[5]
Leu, Leu/Phe[7]

Homocystinuria

Met[1,2,4,6]
Met, Met/Phe, Met/Leu[5]
Met, Met/Phe[7]

Hypermethioninemia

Met[2]
Met, Met/Phe[7]

Citrullinemia

Cit[1,2,6]
Cit/Phe, Cit/Tyr[4]
Cit, Orn/Cit, Cit/Arg[5]
Cit, Cit/Arg[7]

Nonketotic hyperglycinemia

Gly[2,4,5]

Tyrosinemia Type I

[1,4]Met, Tyr
[2,6]Tyr
[7]Tyr, Tyr/Phe

Tyrosinemia II

[2]Tyr
[7]

Argininemia

Arg
[2]Arg, Arg/Orn

PRO Hyperprolinemia

[4]Pro/Phe

HHH

[2]Orn, HomoCit
[7]Orn, Orn/Cit

TABLE 4-continued

Aminoacidopathies 5-oxoprolinuria

[2]5-Oxopro
[4]pyroGlu/Phe
Argininosuccinic aciduria

[1,6]Cit
[4]Cit/Tyr
[5]Asa
[7]Cit, Cit/Arg

TABLE 5

Fatty Acid Oxidation Disorders

SCAD

C4, C6[1]
C4[2,5,7]
C4, C5, C4/C2, C5/C2[4]
C4, C4/C2, C4/C3[6]
MCAD

C8, C10:1[1]
C8, C10, C10:1, C6[2]
C6, C8, C10, C10:1, C8/C10[3]
C6, C8, C10:1[4,7]
C6, C8, C10:1, C10, C8/C2, C8/C10, C8/C12[5]
C6, C8, C10:1, C8/C10[6]
Glutaric acidemia Type II C5DC[1]
C4, C5, C8:1, C8, C12, C14, C16, C5DC[2]
C4, C5DC, C5, C6, C8, C10[3]
C6, C8, C10, C5/C2[4]
C4, C5, C6, C8, C10[6]
C8, C10, C5DC[7]
Carnitine transporter defect

C0, C2[5]
CPT I

C16, C18:1, C18[2]
C0, C16, C18, C0/(C16 + C18)[5]
Ethylmalonic acidemia

C4, C5, C4/C2, C5/C2[4]
2,4 Dienoyl CoA reductase deficiency[6]

C10:2
LCAD

[4]C14:2, C14:1, C14:1/C16
VLCAD

[1]C14, C14:1, C16, C18
[2]C14:1, C14, C16
[3]C14:1, C14, C16:1, C16, C18:1, C18, C14:1/C12:1
[4]C14:2, C14:1, C14:1/C16
[5]C14:1 or C14
[6]C14, C14:1, C14:2, C16:1, C14:1/C16
[7]C14:1
LCHAD

[1]C14, C14:1, C16, C18, C14OH, C14:1OH, C16OH, C18OH
[2]C16OH, C18:1OH, C18OH
[3]C16OH, C18:1OH, C18OH, C16OH/C16
[5]C14OH, C16:1OH, C16OH, C18:1OH, C18:OH, C14:1, C14
[6]C16OH, C18:1, C18:1OH, C18:2, C18:2OH
[7]C16OH
Trifunctional protein deficiency

[2]C16OH, C18:1OH, C18OH
[6]C16OH, C18:1OH, C18OH, C16OH/C16
[5]C14OH, C16:1OH, C16OH, C18:1OH, C18:OH, C14:1, C14

TABLE 5-continued

Fatty Acid Oxidation Disorders

Carnitine/acylcarnitine translocase deficiency

[2]C16, C18:1, C18
[5]C0, C16, C18, C0/(C16 + C18)
[7]C16
CPT II

[1]C14, C14:1, C16, C16:1
[3]C16, C18, C18:1, C16/C14:1
[6]C16, C18:1, C18:2
[7]C16

References for Tables 4 and 5 are as follows: [1] ACMG/ASHG Test and Technology Transfer Committee Working Group, Tandem Mass Spectrometry in Newborn Screening. *Genetics in Medicine* July/August 2000; Vol 2, No. 4; [2] CDC, U.S. Department of Health and Human Services. "Using Tandem Mass Spectrometry for Metabolic Disease Screening Among Newborns." *MMWR* Apr. 13, 2001; Vol. 50, No. RR-3; [3] Chace D H, et al. *Clinical Chemistry* 2001; 47:1166-82; [4] Rashed M S. et al. *Clinical Chemistry* 1997; 43(7):1129-41; [5] Schulze A et al. *Pediatrics* 2003; 111(6):1399-1406; [6] The Wisconsin NBS Laboratory—Wisconsin State Laboratory of Hygiene. "Health Professionals Guide to Newborn Screening." Retrieved Oct. 28, 2003, from the website of The Board of Reagents of the University of Wisconsin System. [7] Zytkovicz T H et al, *Clinical Chemistry* 2001; 47(11):1945-55.

In the methods of the invention, the presence or amount of one or more metabolic analytes can be determined. An amount of a metabolic analyte refers to an absolute amount of a molecule in a sample or to a relative amount of the molecule, including amounts determined under steady-state or non-steady-state conditions. The amount of a metabolic analyte can be determined relative to a reference molecule in a sample.

The methods of the invention involve determining the presence or amount of at least one metabolic analyte and/or product, where the presence or amount of each metabolic analyte and/or product correlates the presence or absence of a metabolic disorder. To quantitate the amount of a metabolic analyte or product in a test sample, an internal standard can be used, as is described below. The methods of the invention can be used quantitatively, if desired, to allow comparison of test sample results with known or pre-determined standard amounts of particular analyte and/or product amounts. The methods of the invention can be used qualitatively when the presence of the metabolic analyte or enzyme in the sample is indicative of a metabolic disorder, for example, when the metabolic analyte detected is the result of abnormal metabolic processes, or when enzyme activity is not detected in a normal sample. The methods can also be used qualitatively when a test sample is compared with a reference sample, which can be either a normal reference or metabolic disorder reference. In this format, the relative amount of analyte or product can be indicative of a metabolic disorder.

An internal standard, or reference analyte, for a metabolic analyte useful in a method of the invention can be any modification or analog of the analyte that is detectable by mass spectrometry. A reference analyte is separately detectable from the metabolic analyte based on a unique physical characteristic, such as a unique mass or charge-to-mass ratio. In addition, a suitable generic reference standard can be used.

Such an internal standard will, for example, co-elute with the analyte or product if a separation method such as chromatography is used prior to mass spectrometric analysis. A commonly used internal standard for mass spectrometry is a stable isotopically labeled form or chemical derivative of the analyte or product. Non-limiting examples of internal standards for metabolic analytes that are amino acids include isotopically labeled amino acids such as $^{15}N,2-^{13}C$-Glycine, $^2H4$-Alanine, $^2H$ 8-Valine, $^2H$ 3-Leucine, $^2H$ 3-Methionine, $^2H$ 5-Phenylalanine, $^2H$ H4-Tyrosine, $^2H$ 3-Aspartate, $^2H$ 3-Glutamate, $^2H2$-Ornithine $^2H$ Cl, $^2H2$-Citrulline, and $^2H$ 4-13C-Arginine•HCl. Non-limiting examples of internal standards for metabolic analytes that are carnitines include isotopically labeled carnitines such as $^2H9$-carnitine, $^2H$ 3-acetylcarnitine, $^2H$ 3-propionylcarnitine, $^2H$ 3-butyrylcarnitine, $^2H$ 9-isovalerylcarnitine, $^2H$ 3-octanoylcarnitine, $^2H$ 9-myristoylcarnitine, and $^2H$ 3-palmitoylcarnitine. An internal standard for an enzymatic product, or reference product, can be any modification or analog of the product that is identifiable by mass spectrometry. A reference product is separately detectable from the product based on a unique physical characteristic, such as a unique mass or charge-to-mass ratio. A non-limiting example of an internal standard for an enzymatic product is an isotopically labeled form of the product, such as a deuterated form of the product.

Generally, a cut-off value for each metabolic analyte or enzyme activity will be known in the art for commonly tested analytes and enzymes. A cut-off value is typically an analyte concentration or enzyme activity, or ratio thereof, above or below which is considered indicative of a metabolic disorder or cause for retest. Thus, in accordance with the present invention a reference level of a metabolic analyte or enzymatic activity (as indicated by presence or amount of enzymatic product) in a particular sample type is identified as a cut-off value, above or below which there is a significant correlation between the presence of the analyte or enzymatic activity and presence or absence of a metabolic disorder. Exemplary cut-off values for amino acid and carnitine/acylcarnitine butyl esters are described in U.S. Pat. No. 6,455,321. Also described are procedures for determining significance of an elevated amount of a metabolic analyte in a blood sample from a newborn. This method can be applied to a variety of types of samples (for example, serum and tissue biopsy) from a subject of any age.

Those of skill in the art will recognize that some cut-off values are not absolute in that clinical correlations are still significant over a range of values on either side of the cutoff; however, it is possible to select an optimal cut-off value (e.g. varying H-scores, and the like) of analyte, enzyme activity for a particular sample types. Cut-off values determined for use in a method of the invention generally are compared with published ranges but can be individualized to the methodology used and patient population. It is understood that improvements in optimal cut-off values could be determined depending on the sophistication of statistical methods used and on the number and source of samples used to determine reference level values for the different analyte, enzyme activity and sample types. Therefore, established cut-off values can be adjusted up or down, on the basis of periodic re-evaluations or changes in methodology or population distribution. In addition, instrument-specific cut-off values can be used, if desired, for example such as when inter-instrument performance comparability is <10%.

The reference level can be determined by a plurality of methods, provided that the resulting reference level accurately provides an amount of metabolic analyte or enzyme activity above which exists a first group of individuals having a different probability of metabolic disorder than that of a second group of individuals having metabolic analyte or enzyme activity amount below the reference level. The reference level can be determined by comparison of metabolic analyte or enzyme activity amount in populations of patients having the same metabolic disorder. This can be accomplished, for example, by histogram analysis, in which an entire cohort of patients are graphically presented, wherein a first axis represents the amount of metabolic analyte or enzyme activity and a second axis represents the number of individuals in the cohort whose sample contain metabolic analyte or enzyme activity at a given amount. Two or more separate groups of individuals can be determined by identification of subsets populations of the cohort which have the same or similar levels of metabolic analyte or enzyme activity. Determination of the reference level can then be made based on an amount which best distinguishes these separate groups. The reference level can be a single number, equally applicable to every individual, or the reference level can vary, according to specific subpopulations of individuals. For example, older individuals might have a different reference level than younger individuals for the same metabolic disorder.

The methods of the invention use mass spectrometry for determining the amount or presence of one more metabolic analytes and at least one metabolically indicative enzyme product. A variety of configurations of mass spectrometers can be used in a method of the invention. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix. Other ionization procedures known in the art include, for example, plasma and glow discharge, plasma desorption ionization, resonance ionization, and secondary ionization.

Electrospray ionization (ESI) has several properties that are useful for the invention described herein. For example, ESI can be used for biological molecules such as polypeptides that are difficult to ionize or vaporize. In addition, the efficiency of ESI can be very high which provides the basis for highly sensitive measurements. Furthermore, ESI produces charged molecules from solution, which is convenient for analyzing tag reporters that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer. This in-line arrangement of a liquid chromatography system and mass spectrometer is sometimes referred to as LC-MS. A LC-MS system can be used, for example, to separate un-cleaved or partially cleaved tag reporters from cleaved tag reporters before mass spectrometry analysis. In addition, chromatography can be used to remove salts or other buffer components from the tag reporter sample before mass spectrometry analysis. For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

A quadrupole mass analyzer, as well as the other mass analyzers described herein, can be programmed to analyze a defined m/z or mass range. This property of mass spectrometers is useful for the invention described herein. Since the mass range of cleaved tag reporters will be known prior to an assay, a mass spectrometer can be programmed to transmit ions of the projected correct mass range while excluding ions of a higher or lower mass range. The ability to select a mass range can decrease the background noise in the assay and thus increase the signal-to-noise ratio. In addition, a defined mass range can be used to exclude analysis of molecules. Therefore, the mass spectrometer can accomplish an inherent separation step as well as detection and identification of analytes.

Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low m/z limitations.

Time-of-flight mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadrupole or ion trap mass analyzers. Also data can be acquired quickly with this type of mass analyzer because no scanning of the mass analyzer is necessary.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisinally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans", of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans. The use of these different tandem mass spectrometry scan procedures can be advantageous when large sets of analytes are measured in a single experiment as with multiplex experiments.

In view of the above, those skilled in the art recognize that different mass spectrometry methods, for example, quadrupole mass spectrometry, ion trap mass spectrometry, time-of-flight mass spectrometry and tandem mass spectrometry, can use various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions. The ability to precisely control the movement of ions in a mass spectrometer allows for greater options in detection protocols which can be advantageous when a large number of analytes, for example, from a multiplex experiment, are being analyzed.

Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1. Those skilled in the art will therefore select a mass spectrometer having a resolution appropriate for the analyte(s) to be detected.

Mass spectrometers can resolve ions with small mass differences and measure the mass of ions with a high degree of accuracy. Therefore, analytes of similar masses can be used together in the same experiment since the mass spectrometer can differentiate the mass of even closely related molecules. The high degree of resolution and mass accuracy achieved using mass spectrometry methods allows the use of large sets of analytes because they can be distinguished from each other.

Additional mass spectrometry methods are well known in the art (see Burlingame et al. *Anal. Chem.* 70:647R-716R (1998); Kinter and Sherman, New York (2000)). Exemplary descriptions of mass spectrometry methods for detecting metabolic analytes include Chace D H, Hillman S L, Van Hove J L K, Naylor E W. *Clin Chem* 1997;43:210613; Rashed M S, Bucknall M P, Little D, et al. *Clin Chem* 1997;43: 112941; Matern D, Strauss A W, Hillman S L, Mayatepek E, Millington D S, Trefz F K. *Pediatr Res* 1999;46:459, and Millington D S, Kodo N, Terada N, Roe D, Chace D H. *International Journal of Mass Spectrometry and Ion Processes* 1991;111:21128.

One or more steps of a method of the invention can be automated, if desired. Those skilled in the art will know how to use autosamplers, liquid handling devices, robots, computers and other routine laboratory instruments for automation.

All journal article, reference, and patent citations provided above, in parentheses or otherwise, whether previously stated or not, are incorporated herein by reference.

It is understood that modifications that do not substantially affect the function of the various embodiments of this invention are also included within the definition of the invention provided herein. Accordingly, the following examples are intended to illustrate but not limit the present invention.

EXAMPLE 1

This example describes simultaneous determination of the amount of a metabolic analyte and an metabolically indicative enzyme product from a patient sample.

The enzyme biotinidase is a known metabolically indicative enzyme for the metabolic disorder termed biotinidase deficiency. In the untreated state, profound biotinidase deficiency in newborns typically is characterized by neurological and skin-related symptoms, such as seizures, hypotonia, and rash, often accompanied by hyperventilation, laryngeal stridor, and apnea. Older children may also have alopecia, ataxia, developmental delay, neurosensory hearing loss, optic atrophy, and recurrent infections. Individuals with partial biotinidase deficiency may have hypotonia, skin rash, and hair loss, particularly during times of stress. Once detected, biotinidase deficiency is often treatable by administration of biotin.

It has been previously established that individuals with profound biotinidase deficiency have <10% of mean normal serum biotinidase activity. Individuals with partial biotinidase deficiency have 10-30% of mean normal serum biotinidase activity. Therefore, it is understood that a decrease in biotinidase activity compared to normal reference level is indicative of biotinidase deficiency.

Acylcarnitines and α-amino acid also were assayed. Different patterns of the plasma acylcarnitine profile can indicate the diagnosis of fatty acid oxidation disorders (MCAD, VLCAD, SCAD, MAD, LCHAD, and CPTII), as well as some organic acidemias (propionic acidemia, methylmalonic acidemia, isovaleric acidemia, glutaric acidemia type I, 3-methylcrotonyl CoA carboxylase deficiency, B-ketothiolase deficiency, etc.). Plasma amino acids analysis will detect specific amino acid disorders such as phenylketonuria (PKU), Maple Syrup Urine Disease (MSUD), urea cycle defects, non-ketotic hyperglycinemia and homocystinuria. This analysis is also indicated in patients with general failure to thrive as an initial screen. For assessment of a metabolic disorder, plasma amino acids are compared to age-matched normal values Activity of the enzyme biotinidase and the amount of the α-amino acid and acylcarnitine analytes were measured simultaneously as follows:

Dried blood samples on paper were each punched into a well of a microwell plate. Each sample was reconstituted with 50 microliter of buffer solution containing isotopically labeled biocytin (the substrate for biotinidase), and the mixture was incubated for 17 hours at 42° C. 140 microliter of methanol containing isotopically labeled internal standards for α-amino acids and acylcarnitines and for the product of the biotinidase reaction were then added, and the plate was shaken for 30 minutes at 27° C. The plate was then covered with aluminum foil and placed on an autosampler. Each processed sample was analyzed by tandem mass spectrometry, and concentrations of biotinidase product, endogenous α-amino acids and endogenous acylcarnitines were quantified based on internal standards.

Tables 6 and 7 show data obtained using the above method, as compared to data obtained using well known mass spectrometry screening methods for metabolic analytes without simultaneously measuring enzyme activity. A slope of one indicates identical results between the compared methods.

TABLE 6

α-Amino acid (AA) comparison:

| AA | SLOPE | R2 |
|---|---|---|
| ALA | 1.04 | 0.9916 |
| ARG | 1.11 | 0.9975 |
| CIT | 1.13 | 0.9912 |
| GLY | 1.36 | 0.9836 |
| LEU | 1.14 | 0.9987 |
| MET | 1.00 | 0.9989 |
| ORN | 1.02 | 0.9951 |
| PHE | 0.99 | 0.9949 |
| TYR | 1.10 | 0.9917 |
| VAL | 1.04 | 0.9836 |
| MEAN | 1.09 | 0.9927 |

TABLE 7

Acylcarnitine comparison:

| AC | SLOPE | R2 |
|---|---|---|
| C0 | 1.05 | 0.9994 |
| C2 | 1.12 | 0.9902 |
| C3 | 1.11 | 0.9915 |
| C4 | 1.10 | 0.9946 |
| C5DC | 0.89 | 0.9641 |
| C6 | 0.99 | 0.9973 |
| C8 | 1.00 | 0.9987 |
| C10 | 1.05 | 0.9987 |
| C12 | 1.01 | 0.9968 |
| C14 | 1.06 | 0.9952 |
| C16 | 1.21 | 0.9837 |
| C18 | 1.16 | 0.9844 |
| MEAN | 1.06 | 0.9912 |

These results show that the above method produces data that correlate with well known mass spectrometry screening methods in which α-amino acids and acylcarnitines are extracted and measured without measuring enzyme activity simultaneously. FIG. 1 shows that the above method produces data that correlate well known enzyme activity screening methods that measure fluorescence of a tagged product without measuring simultaneously concentrations of α-amino acids and acylcarnitines.

EXAMPLE 2

This example describes simultaneous determination of amounts of metabolic analytes and a metabolically indicative enzyme in a reaction mixture that includes one or more protease inhibitors.

To determine affects of including protease inhibitors in assays for simultaneous detection of biotinidase activity, amino acids, acylcarnitines and carnitines, experiments were performed using both non-derivatized and derivatized samples. For non-derivatived samples, dried blood spots were punched (3 mm) and reconstituted with 50 µL Biotinidase buffer (100 nM Ammonium Acetate pH 6.0; 0.128 nM Biocytin (which can be substituted with isotopically labeled biocytin if desired), 0.32 mM dithiothreitol, 6 µM PEPSTATIN protease inhibitor or 1% vol/vol of COMPLETE mini protease inhibitor stock solution (1 tablet in 1.5 ml water)), or both inhibitors, in the presence or absence of AAAC internal standards ((such as deuterium-labeled amino acid(s)). The sample was incubated for 17 hours at 42° C. MeOH (140 µl) was then added to the sample, and the sample was shaken at 650 or 750 rpm (depending on shaker used) for 30 minutes at 27° C. 50 µl of each sample was added a well of a non-derivatized plate (NUNC) containing 140 µL of Amino Acid and Acylcarnitine internal standards (0.05% oxalic acid in 75% MeOH: 25% HPLC grade water, with standards). The plate was shaken for 10 minutes at 27° C. MS/MS analysis proceeded upon removal of the samples from the plate via an autosampler.

For derivatized samples, dried blood spots were punched (3 mm) and reconstituted with 190 µL Biotinidase buffer (100 nM Ammonium Acetate pH 6.0; 0.128 nM Biocytin (which can be substituted with isotopically labeled biocytin if desired), 0.32 mM dithiothreitol, 6 µM PEPSTATIN protease inhibitor or 1% vol/vol of COMPLETE mini protease inhibitor stock solution (1 tablet in 1.5 ml water)), or both inhibitors, in the presence or absence of AAAC internal standards (such as deuterium-labeled amino acid(s)). The sample was incubated for 17 hours at 42° C. MeOH (140 µl) was then added to the sample, and the sample was shaken at 650 or 750 rpm (depending on shaker used) for 30 minutes at 27° C. 50 µl of each sample was added a well of a Derivatized plate (NUNC) containing 140 µL of Amino Acid and Acylcarnitine internal standards (0.05% oxalic acid in 75% MeOH: 25% HPLC grade water). The plate was shaken for 10 minutes at 27° C. Samples were then concentrated to dryness using a SPE Dry Dual Concentrator. N-Butanol/hydrochloric acid (50 µl) was added and the sample was incubated at 60° C. for 30 minutes. Samples were then concentrated to dryness using a SPE Dry Dual Concentrator. Reconstitution was performed by adding 75 µl of 0.1% acetic acid in 80:20 Acetonitrile/water. The sample was shaken at 650 or 750 rpm for 10 minutes at 27° C. MS/MS analysis proceeded upon removal of the samples from the plate via an autosampler.

In this case, internal standard (IS) were added to the Biotinidase assay buffer. Similar results can be obtained when IS are added to wells of the plate prior to sample addition; when IS are added to the sample mixture prior to, or after, derivatizing. Each of these approaches yielded similar results.

Table 9 shows "% recovery" in the presence of absence of protease inhibitor(s), where "% recovery" means the amount of analyte detected experimentally/actual amount of analyte in sample. These results indicated that presence of inhibitors resulted in more accurate determination of most amino acid standards tested.

TABLE 9

|  | Control (conc.) | % Recovery | % Recovery w/Inhibitors |
|---|---|---|---|
| Alanine | 172.2 | 125.7% | 89.6% |
| Arginine | 74.34 | 722.7% | 60.3% |
| Citruline | 54.38 | 149.9% | 127.6% |
| Glycine | 92.96 | 133.4% | 123.6% |
| Leucine | 170.2 | 201.4% | 109.5% |
| Ornithine | 79.84 | 123.8% | 95.7% |
| Oxo-Proline | 16.58 | 245.7% | 199.8%* |
| Phenylalanine | 59.66 | 266.5% | 121.9% |
| Proline | 108.04 | 169.8% | 219.4%* |
| Tyrosine | 52.84 | 244.6% | 99.4% |
| Valine | 204.4 | 164.4% | 94.2% |

What is claimed is:

1. A method for detecting a biotinidase deficiency and one or more disorders selected from: an aminoacidopathy, a fatty acid oxidation disorder and an organic acid disorder, in an individual, comprising:
    (a) contacting a sample comprising:
        (i) biotinidase and
        (ii) one or more amino acids or carnitines,
    with biocytin and one or more protease inhibitors to produce a reaction admixture, under conditions wherein said biotinidase is capable of acting on said biocytin, to generate at least one product, the product selected from biotin and lysine;
    (b) contacting said reaction admixture with a reagent that inhibits the ability of said biotinidase to act on biocytin, wherein said one or more amino acids or carnitines and said at least one product are soluble in said reagent; to produce a test sample and
    (c) determining the amount of said one or more amino acids or carnitines and determining the amount of said at least one product contained in said test sample using mass spectrometry,
    wherein a determined amount of said one or more amino acids or carnitines correlates with presence or absence of said aminoacidopathy, fatty acid oxidation disorder or organic acid disorder and a determined amount of said at least one product correlates with presence or absence of said biotinidase deficiency.

2. The method of claim 1, wherein said sample is a body fluid sample.

3. The method of claim 2, wherein said body fluid sample is blood.

4. The method of claim 1, wherein said sample is dried.

5. The method of claim 1, wherein said individual is a human suspected of having a metabolic disorder.

6. The method of claim 1, wherein said individual is a neonate.

7. The method of claim 1, wherein said individual is a newborn.

8. The method of claim 1, wherein said individual is a child.

9. The method of claim 1, wherein said individual is an adult.

10. The method of claim 1, wherein said one or more disorders is an inborn error of metabolism.

11. The method of claim 1, wherein said one or more disorders is an acquired metabolic disorder.

12. The method of claim 1, wherein said one or more carnitines is an acylcarnitine or plurality of acylcarnitines.

13. The method of claim 1, wherein step (a) further comprises contacting said sample with an internal standard corresponding to biocytin.

14. The method of claim 1, wherein step (b) further comprises contacting said sample with at least one internal standard product corresponding to the at least one product contained in said sample.

15. The method of claim 1, wherein step (b) further comprises, prior to determining, adding one or more internal standard amino acids or carnitines corresponding to the one or more amino acids or carnitines contained in said sample.

16. The method of claim 1, wherein said mass spectrometry is tandem mass spectrometry.

17. The method of claim 1, wherein one of said protease inhibitors is a protease cocktail.

18. The method of claim 1, wherein one of said protease inhibitors is PEPSTATIN.

19. The method of claim 1, wherein said reaction admixture is aqueous.

20. The method of claim 19, wherein said reagent is non-aqueous.

21. The method of claim 20, wherein said reagent comprises an alcohol.

22. The method of claim 21, wherein said reagent is methanol.

23. The method of claim 20, wherein said reagent comprises aorganic solvent.

* * * * *